(12) United States Patent
Pan et al.

(10) Patent No.: US 7,785,832 B2
(45) Date of Patent: Aug. 31, 2010

(54) METHOD OF PROTEIN SYNTHESIS

(75) Inventors: Jae-Gu Pan, Daejeon (KR);
Heung-Chae Jung, Daejeon (KR);
Sooan Shin, Daejeon (KR)

(73) Assignee: HALLA Patent & Law Firm, Seoul (KR)

( * ) Notice: Subject to any disclaimer, the term of this patent is extended or adjusted under 35 U.S.C. 154(b) by 853 days.

(21) Appl. No.: 11/335,592

(22) Filed: Jan. 20, 2006

(65) Prior Publication Data

US 2006/0141578 A1    Jun. 29, 2006

Related U.S. Application Data

(63) Continuation-in-part of application No. 10/608,078, filed on Jun. 30, 2003, now abandoned, which is a continuation of application No. 09/946,376, filed on Sep. 5, 2001, now abandoned.

(30) Foreign Application Priority Data

May 9, 2000    (KR) .......................... 10-2000-52464

(51) Int. Cl.
*C12P 21/00* (2006.01)
*C07H 21/04* (2006.01)
(52) U.S. Cl. ..................................... 435/69.1; 536/23.1
(58) Field of Classification Search ....................... None
See application file for complete search history.

(56) References Cited

OTHER PUBLICATIONS

Shin et al., FEMS Microbiology Letters 146: 103-108, 1997.*

* cited by examiner

*Primary Examiner*—Eileen B O'Hara
(74) *Attorney, Agent, or Firm*—Jones Day

(57) ABSTRACT

The present invention relates to a method of protein synthesis and, more particularly, to a method of effective protein synthesis by regulating the expression of a protein in a host cell, wherein said host cell is transformed with an expression vector comprising a promoter as well as a DNA fragment for a gene that encodes a desired protein, wherein said promoter has an inductive activity for transcription during the resting stage of cell growth and also the induction of said protein expression can be controlled by varying culturing conditions.

8 Claims, 12 Drawing Sheets

(a)

(b)

(c)

METHOD OF PROTEIN SYNTHESIS

This application is a continuation-in-part of application Ser. No. 10/608,078, filed Jun. 30, 2003, now abandoned, which is a continuation of application Ser. No. 09/946,376, filed Sep. 5, 2001, now abandoned, which claims priority to Korean patent application 00-52454.

FIELD OF THE INVENTION

The present invention relates to a method of protein production and, more particularly, to a method of effective protein production by regulating the expression of a protein in a host cell, wherein the host cell is transformed with an expression vector comprising a promoter as well as a DNA fragment for a gene that encodes a desired protein, wherein the promoter is active at the resting stage of the culture and also the induction of said protein expression can be controlled by varying culturing conditions. The constructed expression vector is very effective for production of desired target proteins in high cell density culture greater than 40 g/L.

BACKGROUND OF THE INVENTION

Protein synthesis via a microbial organism can be regulated mostly at the level of transcription and thus the selection of a most appropriate promoter that can strongly direct the synthesis of a desired protein is very important (Markrides, 1996, *Microbial Reviews*, 60, 512-538).

There are several factors that should be considered in selecting such a strong promoter. First, the promoter should have a very active transcriptional activity to synthesize sufficient amount of mRNA. Second, the promoter should be able to well control the protein expression, however, the promoter should not have any transcriptional activity or it should be kept at an extremely low level, if at all, prior to the induction of a given protein expression. Third, the promoter should be well transformed into a host cell. Finally, the promoter should have a relatively easy induction system for protein expression and is also preferred to be cost-effective.

There are a number of promoters that have been used in constructing recombinant expression vectors for protein biosynthesis using *E. coli* as a host cell; e.g., lac promoter (Roberts et al., 1979, *Proc. Natl. Acad. Sci. USA*, 76, 760-764), tac promoter (Aman et al., 1983, *Gene*, 25, 167-178), trc promoter (Brosius et al., 1985, *J. Biol. Chem.*, 260, 3539-3541), PL or PR promoter (Elvin et al., 1990, *Gene*, 87, 123-126), and T7 promoter (Studier et al., 1986, *J. Mol. Biol.;*, 189, 113-130). These promoters are well known to exhibit very strong transcriptional activities in the presence of a particular inducer and accumulate more than 10-30% of the total proteins in cells. However, these promoters are considered disadvantageous in that their transcriptional activities are maintained at a relatively high level when cells are at a normal growth stage. Further, recombinant expression systems utilizing lac promoter or promoters derived from lambda phage are very effective and convenient in culturing *E. coli* for a general laboratory scale use, however, they are not well suited for production in the large culture. Still further, expression systems with lac promoter use isopropyl-β-D-thiogalactoside (IFTG) as an inducer, a highly expensive compound, and thus it becomes quite costly to prepare a large-scale cell culture. In case of an expression system using a promoter derived from lambda phage, it is required to increase a temperature for the expression of a protein and this increase in temperature results in generation of inactive inclusion bodies. Also, uniform temperature condition can be hardly maintained within a culture when preparing a large-scale culture.

Various efforts have been reported to solve the above-mentioned problems; e.g., phoA promoter (Miyake et al., 1985, *J. Biochem.*, 97, 1429-436), cst-1 promoter (Turner et al., 1992, *Biotechnol. Bioengin.*, 40, 271-79), nar promoter (Lee et al., 1996, *Biotechnol. Lett.*, 18, 129-134), and trp promoter (Yansura et al., 1990, *Methods. Enzymol.*, 185, 54-0). However, these promoters are not advantageous in that the regulation of expression is very complicated and inefficient.

Another important issue in recombinant protein expression might be a method of easy cultivation of host cells and easy induction of target proteins. One of such efforts is the use of modified specific medium for automatic induction (Studier, FW, 2005, Protein production by auto-induction in high density shaking cultures, *Protein Expr Purif*, 41(1):207-234). However, the promoters used were still strong ones of T7 and tac. Therefore, it has been an urgent need to develop a method for easy induction of automatic initiation of synthesis of target proteins.

SUMMARY OF THE INVENTION

To solve the above problems, the inventors of the present invention focused their studies on developing a protein expression system with great efficiency and convenience and the biosynthesis of a protein using this system thereof. As a result, the inventors invented a novel protein expression method creating a expression vector having a promoter which has a transcriptional activity during the resting stage of the cell culture so that protein expression can be induced only at the resting stage of the culture, and also the transcription can be induced in the presence of an organic acid in the culture medium such as acetic acid or succinic acid.

Therefore, the object of the present invention is to provide a new method of protein synthesis by means of a protein expression system which is characterized in that the system contains a promoter which has a transcriptional activity during the resting stage of cell culture and also a protein expression is regulated with ease as well as efficiency.

Another object of the present invention is to provide a recombinant vector comprising a gene that encodes a desired protein and a promoter which has an inductive activity for transcription during the resting stage of cell growth, wherein the transcription is induced by an organic acid compound.

Yet, another object of the present invention is to provide a recombinant transformant containing the said vector directing a desired protein synthesis.

Yet, another object of the present invention is to provide a method of culturing host cells in order to automatically induce target proteins in host cells.

Yet, another object of the present invention is to provide the expression vectors containing an artificially constructed protomters consisting of tamdemly repeated promoters which are active at the resting stage of the culture.

DETAILED DESCRIPTION OF THE PREFERRED EMBODIMENTS

Figure 1:
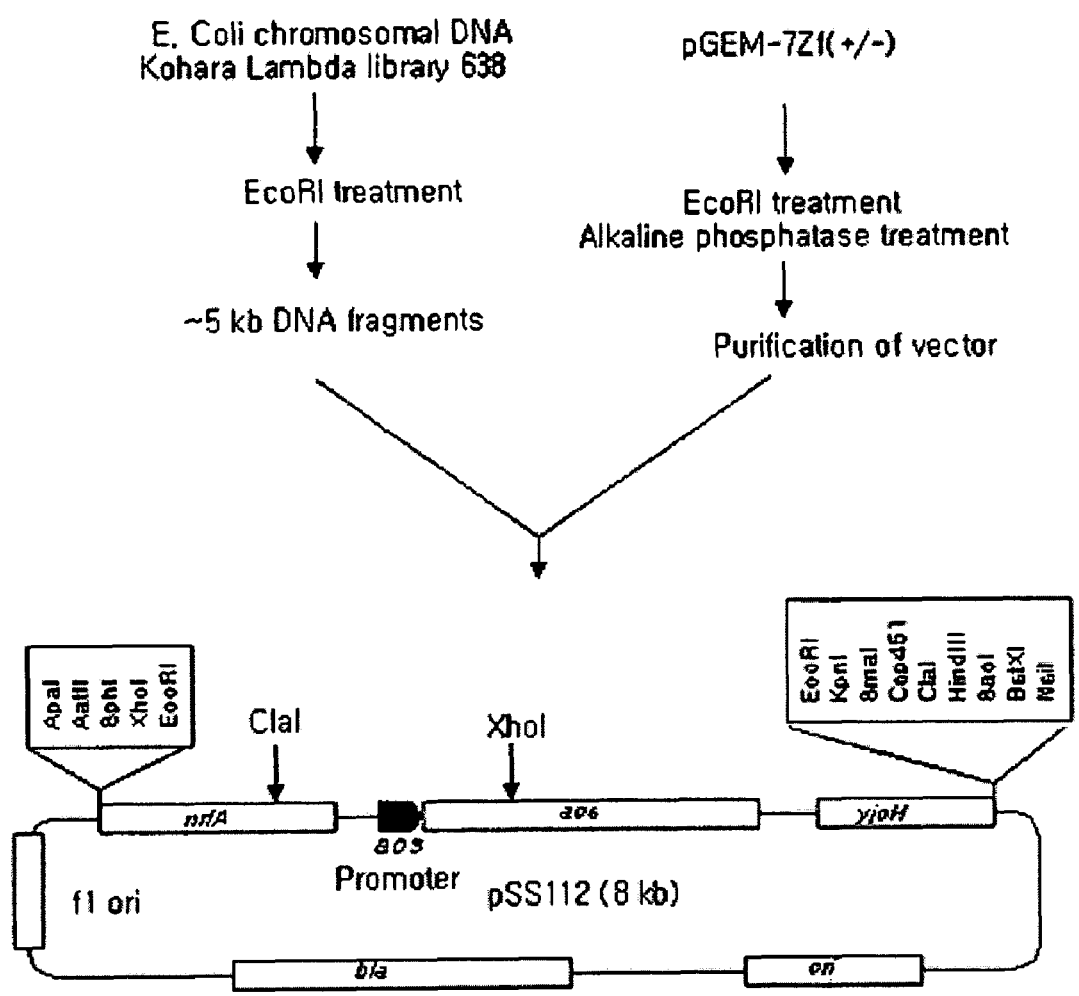
FIG. 1 is a schematic diagram showing the process of constructing pSS112, an expression vector, according to the Example 1 of the present invention wherein a DNA fragment that includes an acs gene and its promoter obtained from Kohara lambda library 638 of *E. coli* chromosome subcloned into pGEM-7fz(+/−).

The present invention relates to a method of producing a desired protein by gene recombination comprising:
(a) constructing a gene expression vector comprising a gene that encodes the desired protein and a promoter which has an inductive activity for transcription during the resting stage of cell growth, wherein the transcription is induced by an organic acid;
(b) introducing a gene expression vector into a host cell;
(c) inducing the expression of the desired protein by culturing the host cell in a culture medium; and
(d) recovering the desired protein.

The present invention is described in detail as set forth hereunder.

The inventors of the present invention, considering the importance of selection of a suitable promoter in protein expression technology, studied acs promoter of E. coli based on the report by Kumari et al. (Kumari et al, 1995, J. Bacteriol., 177, 2878-2886) and subsequently revealed that the expression of acs promoter is inhibited by the glucose present in the culture medium but induced by acetic acid, and this kind of induction of expression is regulated during the stationary phase of cell culture (Shin et al, 1997, FEMS Microbiology Letters, 146, 103-08; Kumari et al., 2000, J. Bacteriol., 182(2):551-554).

The inventors of the present invention introduced acs promoter into an expression system in order to utilize the advantage of a promoter that has a transcriptional activity during the resting stage of a host cell growth. A process of cell growth can be distinguished from a process of protein expression when such a promoter is used. By differentiating these two processes, an optimized culturing strategy most suitable for each process can be established. In addition, protein expression can be induced by culturing host cells at a high concentration resulting in a more efficient protein synthesis.

For the expression of a protein during the resting stage of a host cell growth, it is required to provide an appropriate level of energy as well as a method toward a long-term protein synthesis, and the recent high protein expression system during the resting stage of a host cell growth suggested a good resolution to overcome the long-awaited problem (Rowe & Summers, 1999, Appl. Environ. Microbiol., 65, 2710-2715).

The method of constructing a recombinant expression vector according to the present invention is described in detail as described below.

First, a promoter the transcription of which can be induced by an organic acid such as acetic acid or succinic acid should be obtained. The promoter of the present invention is characterized in that it includes a DNA fragment of the acs gene of E. coli, a DNA fragment that has a nucleotide sequence partially identical to that of the acs gene of E. coli, or a DNA fragment whose biological function is similar to that of the acs gene of E. coli. The transcriptional regulatory region of the acs gene of E. coli is present up to 391 bp upstream of the translational start codon and is located between nrfA and acs genes (Kumari et al., 2000, J. Bacteriol., 182(2):551-554). Further, acs promoters derived from bacteria other than E. coli, fungi, yeasts or actinomyces can also be used if they serve the same function.

Second, it is required to obtain a DNA fragment that encodes a useful protein by using a conventional method. The DNA fragments used in the present invention include those which contain acs gene that encodes acetyl Co A synthetase, lac Z gene that encodes β-galactosidase, chiA gene that encodes chitinase, tliA gene that encodes lipase and other DNA fragments which contain genes for proteins that need to be expressed for conventional purposes can be also utilized. The desired proteins expressed by the present invention could be one selected from the group consisting of hormones, hormone analogs, enzymes, enzyme inhibitors, receptors or their fragments, antibodies or their fragments, single-chain antibodies, structural proteins, toxin proteins, and plant defense-inducing molecules.

Third, it is required to construct a recombinant expression vector by ligating the above promoter and a foreign protein by a conventional recombinant DNA technology so that the selected foreign protein can be exclusively or almost exclusively expressed by the promoter.

Fourth, it is required to transform thus constructed expression vector into a host cell for stability purpose. The host cells that can be used in the present invention are bacteria that belong to Gram-negative bacteria. Particularly, the host cells could be *Enterobacteriaceae* such as *E. coli*. The transformed host cells are cultured by using a conventional method.

The present invention provides a method to effectively synthesize a protein by regulating the expression of the above expression system depending on the various culturing conditions. That is, the present invention is well characterized in that it can easily regulate the expression of a foreign protein by means of a culture medium unlike the conventional methods, which use IPTG as an inducer or increases temperature. The culture media to be used are selected from the group consisting of a complex medium, a minimal culture medium containing acetic acid or succinic acid as a sole carbon source, or a minimal medium containing glucose or glycerol as a sole carbon source.

The preferred examples of methods to induce the expression of foreign proteins using the above-mentioned culture media include:
(a) a method to induce a constituitive expression by culturing a transformed host cell in a complex medium containing yeast extract, peptone, amino acids, vitamins, etc., without using an inducer;
(b) a method to induce a constituitive expression during the cell growth stage or the resting stage of a host cell growth by culturing a transformed host cell in a minimal medium containing acetic acid or succinic acid as a sole carbon source without using an inducer;
(c) a method to induce an expression by culturing a transformed host cell in a minimal medium containing glucose or glycerol as a sole carbon source by adding an organic acid acetic acid or succinic acid as an inducer during a desired stage of cell growth; and
(d) a method to induce a spontaneous expression during the resting stage of cell growth by culturing a transformed host cell in a minimal medium containing a sugar such as glucose or glycerol as a sole carbon source without using an inducer.

As described above, an organic acid such as acetic acid or succinic acid can serve as an inducer for protein expression from the early stage of culture by using these as a carbon source (b), or alternatively by initially culturing in a medium wherein no or an extremely low amount of an organic acid is contained and then adding 0.01%-0.5% (w/v) of the above organic acid at a later desired stage thus inducing the expression of a foreign protein (c). The examples of an inducer that can be used for the expression, in addition to acetic acid or succinic acid, are organic acid compounds such as maleic acid, fumaric acid, and citric acid.

When using glucose as a carbon source, the expression of a foreign protein is inhibited during the cell growth stage, and acetic acid, a byproduct from a cell growth stage, serves as an inducer for expression by maintaining a cell culture for over 24 hr (d). The examples of a sugar that can be used in the medium for the expression, in addition to glucose, are sugars for fermentation carbon and energy sources such as glycerol, fructose and maltose.

The above complex media include LB medium and other conventional media such as YT medium (tryptone, 8 g/L; yeast extract, 5 g/L; NaCl, 5 g/L), 2X YT medium, B broth or tryptone broth (tryptone, 10 g/L; NaCl, 8 g/L), Luria broth (tryptone, 10 g/L; yeast extract, 5 g/L; NaCl, 0.5 g/L), and the above minimal media are M9 minimal medium, M63 minimal medium ($KH_2PO_4$, 13.6 g/L; $(NH_4)_2SO_4$, 2 g/L; $FeSO_4 \cdot 7H_2O$, 0.5 mg/L; adjust to pH 7.0 using KOH).

The advantages of the protein expression according to the present invention can be summarized as follows.

First, the inducers of the present invention are much cheaper than IPTG and thus the present invention is cost-effective. Second, there are various kinds of inducers; inducers are not much affected by the impurities in performing the desired induction; and also instant induction of expression in a large-scale cell culture is also possible. Third, the expression can be carried out in the absence of a particular inducer during the resting stage of cell growth; in particular, the expression during the resting stage of cell growth is advantageous in that more soluble proteins can be expressed by inhibiting the generation of inclusion bodies resulted from overexpression of a given protein. Besides, a precise control of inhibition or regulation of expression is also possible.

In the present invention, the protein expression is proceded using a conventional method while still preserving their own activities of expressed proteins, and the process is completed by passing through separation and purification.

For the production of recombinant proteins in microorganisms, high cell density culture of host cells is a prerequisite for high productivity because the overall process productivity (gram proteins/liter hour) depends upon the cell concentration of host cells (gram cells/liter) and specific production rate (gram proteins/gram cells hour). Therefore, it is necessary to increase the cell concentration of host cells in the culture for relatively high productivity. However, where strong promoters such as T7, tac or their derivatives are used, induction by chemical inducer such as IPTG often results in a relatively low cell concentration. In the present invention, by using the stationary phase active promoter, a relatively high level of expression (up to 1 g/L) was achieved. Thus, the present invention provides a method for obtaining a high level expression of target proteins at high host cell density (greater than 40 g/L of host cells).

Hereunder is given a detailed description of the present invention using the following examples, however, it is appreciated by those skilled in the art that the present disclosure of the preferred form has been made only by way of examples and that numerous changes in the details of the construction, combination, and arrangement of parts may be resorted to without departing from the spirit and scope of the invention. In particular, those proteins as acetyl Co-A (ACS), β-galactosidase (Lac Z), chitinase (Chi A) and lipase (Tli A) used as target proteins are only several examples for the completion of the present invention and they should not be construed as limiting the scope of the present invention.

EXAMPLE

The materials and methods used in the examples of the present invention are as set forth hereunder.

First, *E. coli* JM109 was used as a host cell and pGEM-7Zf (+/−) (Promega, USA), pBluscript II-KS(+/−) (Stratagene, USA), pTrc99A (Pharmacia, Sweden) and pRS41 (Simons et al., 1987, *Gene*, 53, 85-96) were used in subcloning acs promoter.

Second, LB medium (yeast extract 5 g/L, bactotryptone 10 g/L, NaCl 5 g/L, pH 7.2) was used as a basic complex medium, and acetic acid, succinic acid and glucose were added at the concentration of 0.2 (w/v) to the M9 minimal medium ($Na_2HPO_4$ 6 g/L, $KH_3PO_4$ 3 g/L, NaCl 0.5 g/L, $NH_4Cl$ 1 g/L, and add 10 mL of 0.01M $CaCl_2$ after vapor sterilization, pH 7.2) when using one of those as a carbon source. When necessary, antibiotics of ampicillin and tetracycline were used at the concentration of 100 µg/mL and 15 µg/mL, respectively, and cells were cultured at 37° C.

LB culture medium was prepared by using GIBCO BRL LB broth base (Cat. 12780-052, Life Technologies Co., Ltd., USA) and M9 medium was prepared by using M9 minimal salt (Cat. M6030, Sigma Co, Ltd., USA).

Enzymes including restriction enzymes used in DNA cloning were purchased from Korea Postech Co., Ltd. and T4 ligase used was purchased from Boeringer-Mannheim Co., Ltd. (Germany). Desired DNA fragments were recovered from agarose gels by using QiaEx II Gel Extraction Kit (Qiagen Co., Ltd., Germany).

The methods used in the present invention for the manipulation of recombinant DNA and the analysis of total proteins produced by cells were performed according to the methods described in 'Molecular Cloning' by Sambrook et al (A Laboratory Manual, 3rd ed., 2001, Cold Spring Harbor Laboratory Press, USA), unless otherwise specified.

Soluble and insoluble cellular proteins were isolated as follows. First, 1 mL of E. coli cell culture was centrifuged at 12000 rpm for 5 min, and the resulting pellet was washed with 0.85% (w/v) a saline solution and resuspended in a cell-homogenizing buffer solution [50 mM Tris-Cl (pH 8.0), 1 mM PMSF (phenylmethanesulfonyl fluoride)]. The resuspended cells were then homogenized using an ultrasonic cell-homogenizer and centrifuged at 12,000 rpm for 10 min. The resulting supernatant was analyzed as a source for a soluble protein while the lower fraction was analyzed as a source for an insoluble protein.

Example 1

Construction of pSS112 having an E. coli DNA Fragment for Acetyl Co-A Synthetase Gene (acs) and acs Promoter Kohara lambda library no. 638 (Kohara et al., 1989, Cell, 50, 495-508), a known E. coli chromosome library, was used as a DNA fragment for acs gene and acs promoter. The DNA fragment was digested with EcoRI and a resulting DNA fragment about 5 kb in size was separated out and subcloned into pGEM-7Zf(+/−) (Promega, USA), which was also digested with EcoRI, to construct pSS112 (FIG. 1). JM 109, an E. coli cell line, was transformed by using thus constructed pSS112, and the transformed JM109/pSS112 was cordially deposited with the Korea Research Institute of Bioscience and Biotechnology Korean Collection for type cultures, Korean Deposit Associates, located in #52, Oun-dong, Yusung-gu, Daejon, 305-333, Republic of Korea, on Oct. 21, 1999, under Deposit Accession Number KCTC 067BP.

Example 2

Method of Acetyl Co-A Synthetase (ACS) Via acs Promoter

Figure 2:
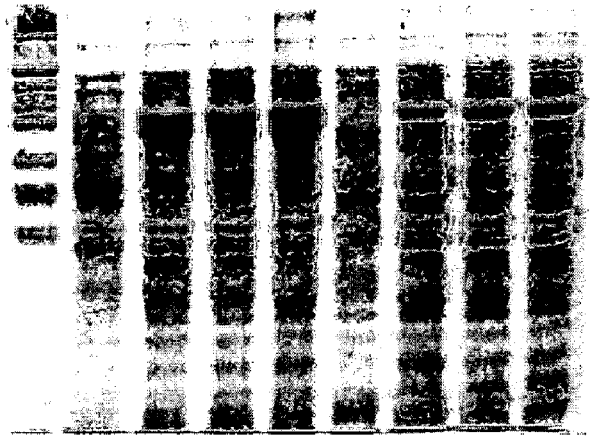
FIG. 2a shows the results of SDS-PAGE for total cumulative acs proteins synthesized by the transformant JM109/ ps112.
FIG. 2b shows the results of SDS-PAGE for a soluble protein fraction.
FIG. 2c shows the results of SDS-PAGE for an insoluble protein fraction.
Figure 2:
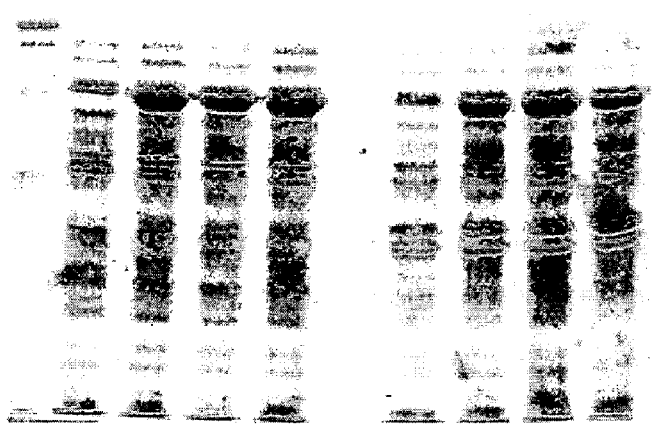
Figure 2:
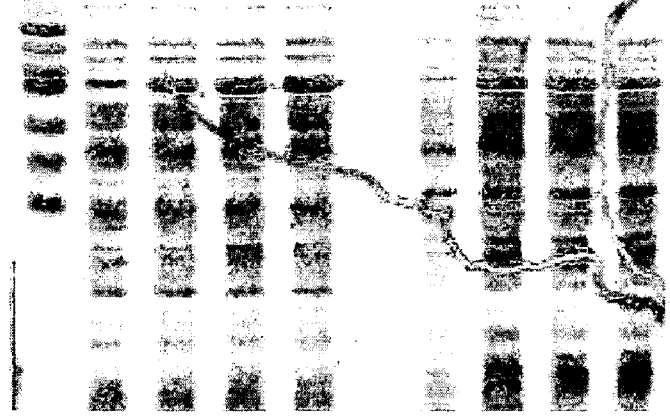

Since pSS112 contains a gene that encodes acetyl Co-A synthetase and a promoter that is involved in the expression of the acetyl Co-A synthetase, this Example focused on the confirmation of the expression of acetyl Co-A synthetase by culturing the transformant JM109/pSS112 in LB medium, a complex medium, or in semi-synthetic M9 minimal culture medium containing 0.2% (w/v) casaminoacid and 0.2% (w/v) glucose at 37° C. (FIG. 2). The result of protein expression was analyzed in SDS-PAGE; more specifically, FIG. 2(a) shows the total cumulative proteins synthesized by the transformant JM109/pSS112, FIG. 2(b) shows the result for a soluble protein fraction and FIG. 2(c) shows the result for an insoluble protein fraction.

Here, M is a protein size marker, 1 represents the analysis for a sample obtained from a 4 hr culture in LB medium, 2 for a sample obtained from a 7 hr culture in LB medium, 3 for a sample obtained from an 11.2 hr culture in LB medium, 4 for a sample obtained from a 22 hr culture in LB medium, 5 for a sample obtained from a 4 hr culture in M9 succinic medium, 6 for a sample obtained from a 7 hr culture in M9 succinic medium, 7 for a sample obtained from an 11.2 hr culture in M9 succinic medium, and 8 for a sample obtained from a 22 hr culture in M9 succinic medium.

The protein ACS, expressed by its own promoter without any chemical inducer or a temperature increase, was expressed at an extremely low level during the first 4 hr of the log phase of cell growth when cultured in LB medium, however, the expression was drastically raised during resting stage by reaching almost 40% of the total protein. When cultured in semi-synthetic M9 minimal medium having glucose as a carbon source, the expression of ACS protein was kept at a low level during the log phase of cell growth and about 28% of the total protein was accumulated within a cell during the resting stage. Therefore, it is shown that all the proteins expressed by acs promoter undergo a large-scale cell culture expression during the resting stage of cell growth.

Example 3

Construction of pSS121

Figure 3:
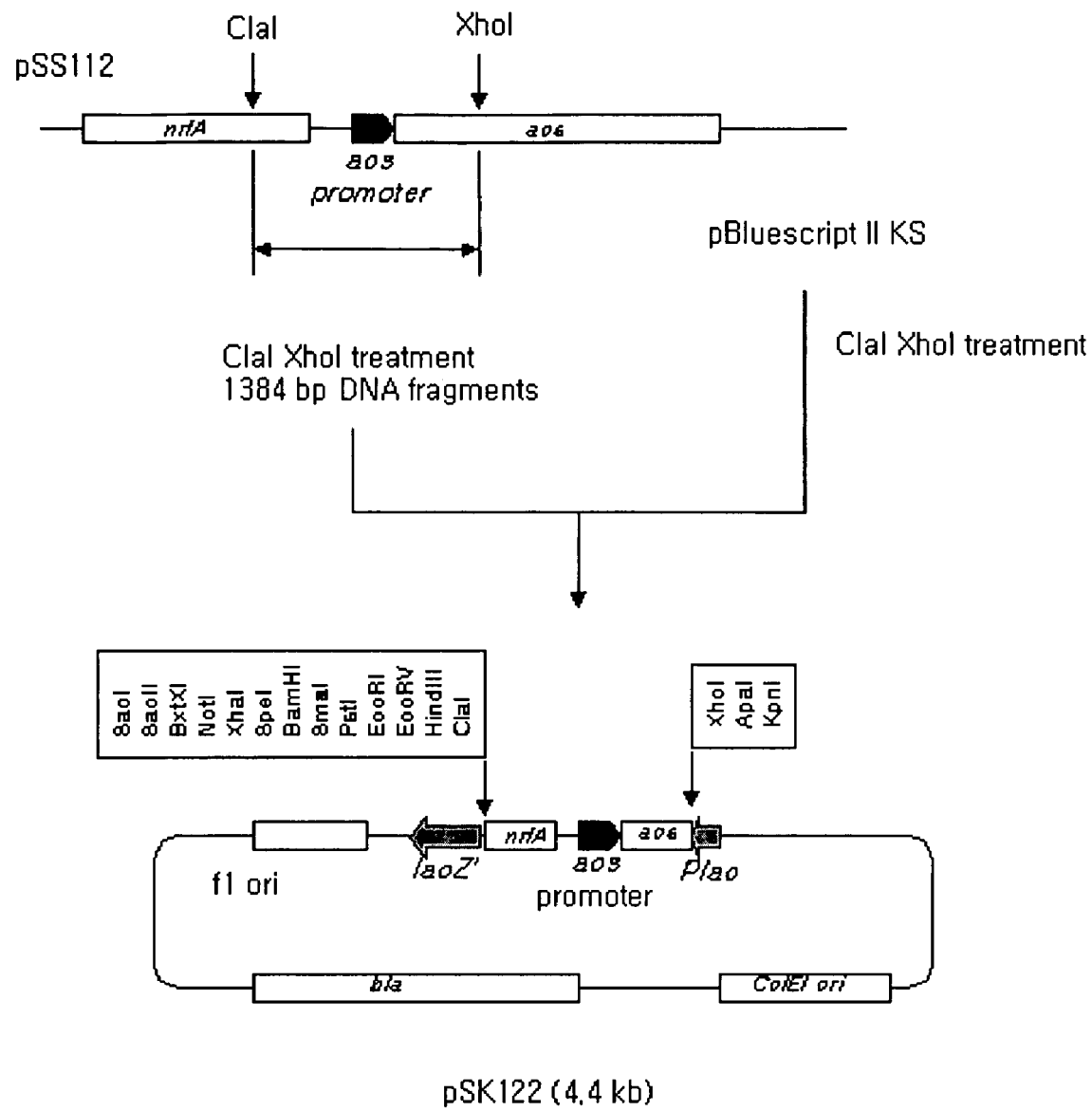
FIG. 3 is a schematic diagram showing the process of constructing pSK122(4.4 kb) according to the Example 3 of the present invention, wherein a 1384 bp DNA fragment with an acs promoter region as well as a region that encodes the beginning part of acs gene is cleaved out from pSS112 and subcloned into pBluescript II KS(+/−).
Figure 4:
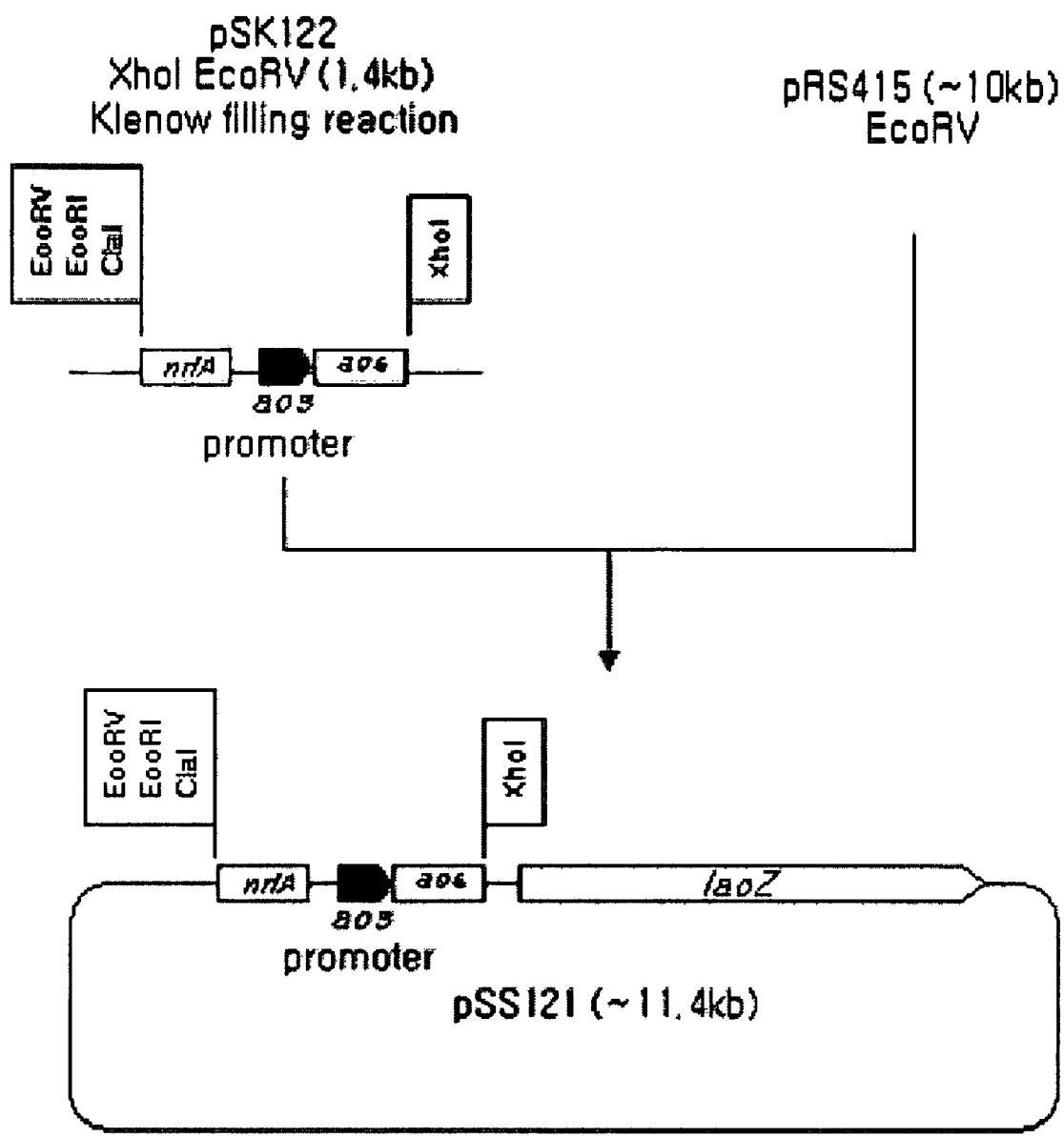
FIG. 4 is a schematic diagram showing the process of constructing pSS121(about 11.4 kb) according to the Example 3 of the present invention, wherein a XhoI-EcoRV DNA fragment of the pSK122 in FIG. 3 is cleaved out, filled in by Klenow filling reaction and is then subcloned into pRS415.

For the expression of β-galactosidase, a protein often used for test of expression, pSS121 was constructed as described below (FIGS. 3 and 4). A DNA fragment containing acs promoter, a 1384 bp fragment of pSS112 digested with Cla I and XhoI, was subcloned into pBluescript II (KS), which was also digested with the same restriction enzymes, and pSK122 was subsequently constructed. Here, the promoter region of pSK122 (SEQ ID NO:1) was sequenced to analyze the sequences of both the 5'strand and the 3'strand of pSK122 by using KS primer (SEQ ID NO:2) and SK primer (SEQ ID NO:3), respectively (Stratagene Co., Ltd., USA). Sequence analysis reaction was performed by using Big Dye Terminater Sequencing Kit (Perkin Elmer Co., Ltd., USA) and the result was analyzed by using a sequence analyzer (Model 377, Stratagene Co., Ltd., USA) and this sequence reading was repeated three times for more accurate identification of given sequences. Then, pSK122 was digested with XhoI and EcoRV, and the digested DNA fragments became blunt-ended by Klenow filling reaction. A 1.34 kb DNA fragment was isolated, purified and subcloned into pRS415, which was digested with EcoRV. A plasmid comprising acs promoter and β-galactosidase gene in this order was selected by a restriction map and was named pSS121 accordingly. Therefore, pSS121 became a plasmid vector having a genetic structure wherein the expression of lac Z gene can be induced by acs promoter. Finally, JM 109, an E. coli cell line, was transformed by using thus constructed pSS121, and the transformed JM109/pSS121 was cordially deposited with the Korea Research Institute of Bioscience and Biotechnology Korean Collection for type cultures, Korean Deposit Associates, located in #52, Oun-dong, Yusung-gu, Daejon, 305-333, Republic of Korea, on Oct. 21, 1999, under Deposit Accession Number KCTC 0675BP.

Example 4

High Expression of β-Galactosidase by acs Promoter

Figure 5:
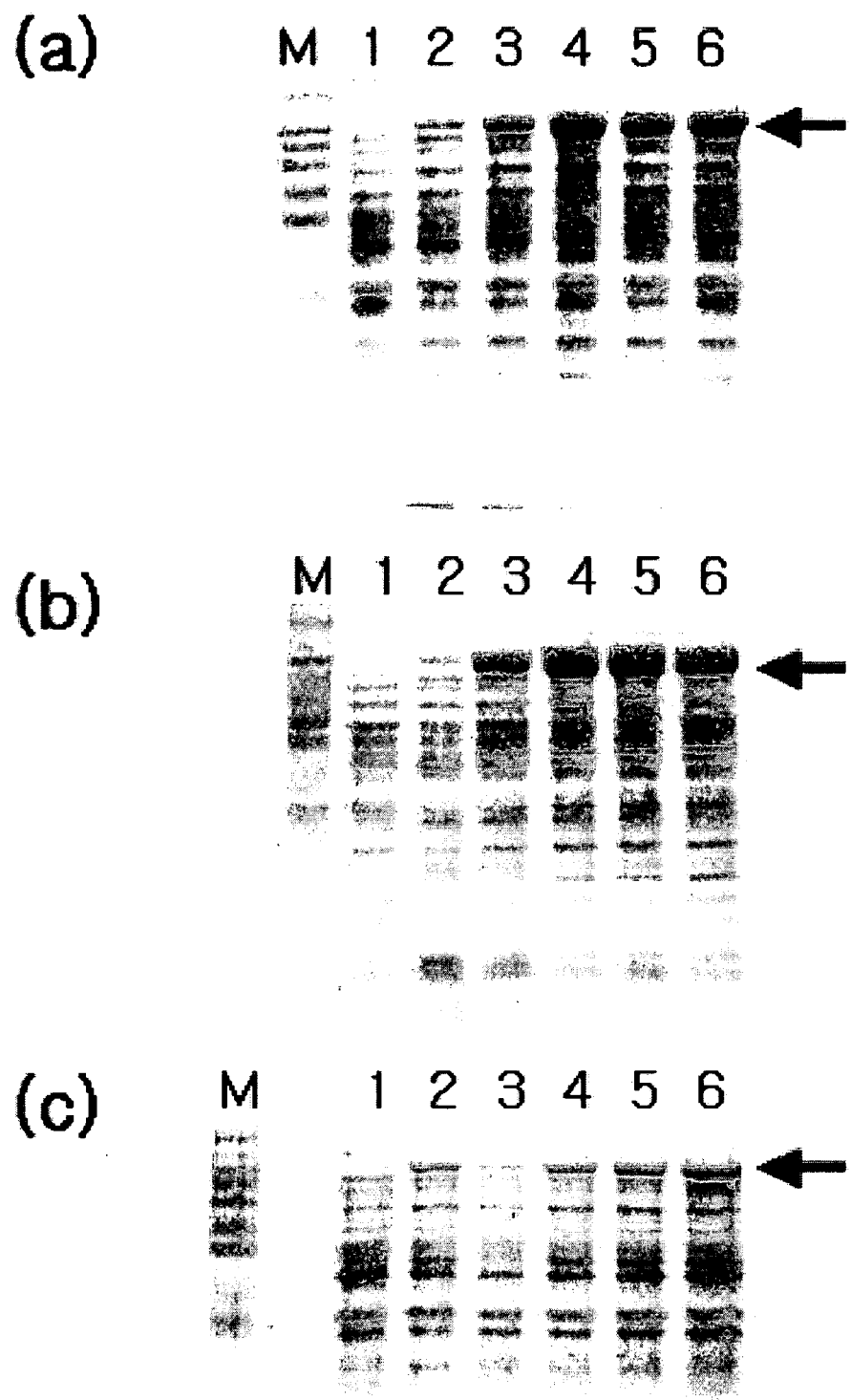
FIG. 5a shows the results of SODS-PAGE for total cumulative β-glycosidase proteins synthesized by the induction of the aces promoter in JM109/ps112.
FIG. 5b shows the results of SDS-PAGE for a soluble protein fraction.
FIG. 5c shows the results of SDS-PAGE for an insoluble protein fraction.

JM109/pSS121, an *E. coli* cell line transformed with pSS121, was cultured in LB medium, a complex medium, and the protein expression was performed as in Example 2 during the resting stage of cell growth. As a result, the level of β-galactosidase synthesis induced by acs promoter was analyzed on SDS-PAGE (FIG. 5). FIG. 5(a) shows the total cumulative proteins synthesized by the recombinant JM109/pSS112, FIG. 5(b) shows the result for a soluble protein fraction and FIG. 5(c) shows the result for an insoluble protein fraction.

Here, M is a protein size marker, 1 represents a sample of the total protein of JM109, 2 for a sample obtained from a 4 hr culture of JM109/pSS112 in LB medium, 3 for a sample obtained from a 6.5 hr culture in LB medium, 4 for a sample obtained from a 9 hr culture in LB medium, 5 for a sample obtained from an 11 hr culture in LB medium, and 6 for a sample obtained from a 24 culture in LB medium.

As shown in FIG. 5, more amount of the enzyme, β-galactosidase, was expressed during the resting stage (after 9 hr), than during the first 4 hr of log phase and the amount of protein expression accounted for approximately 50% of the total cellular protein. When the expressed proteins were fractionized into a soluble protein and an insoluble protein, it was shown that most proteins were expressed in cells in a soluble form.

Figure 6:
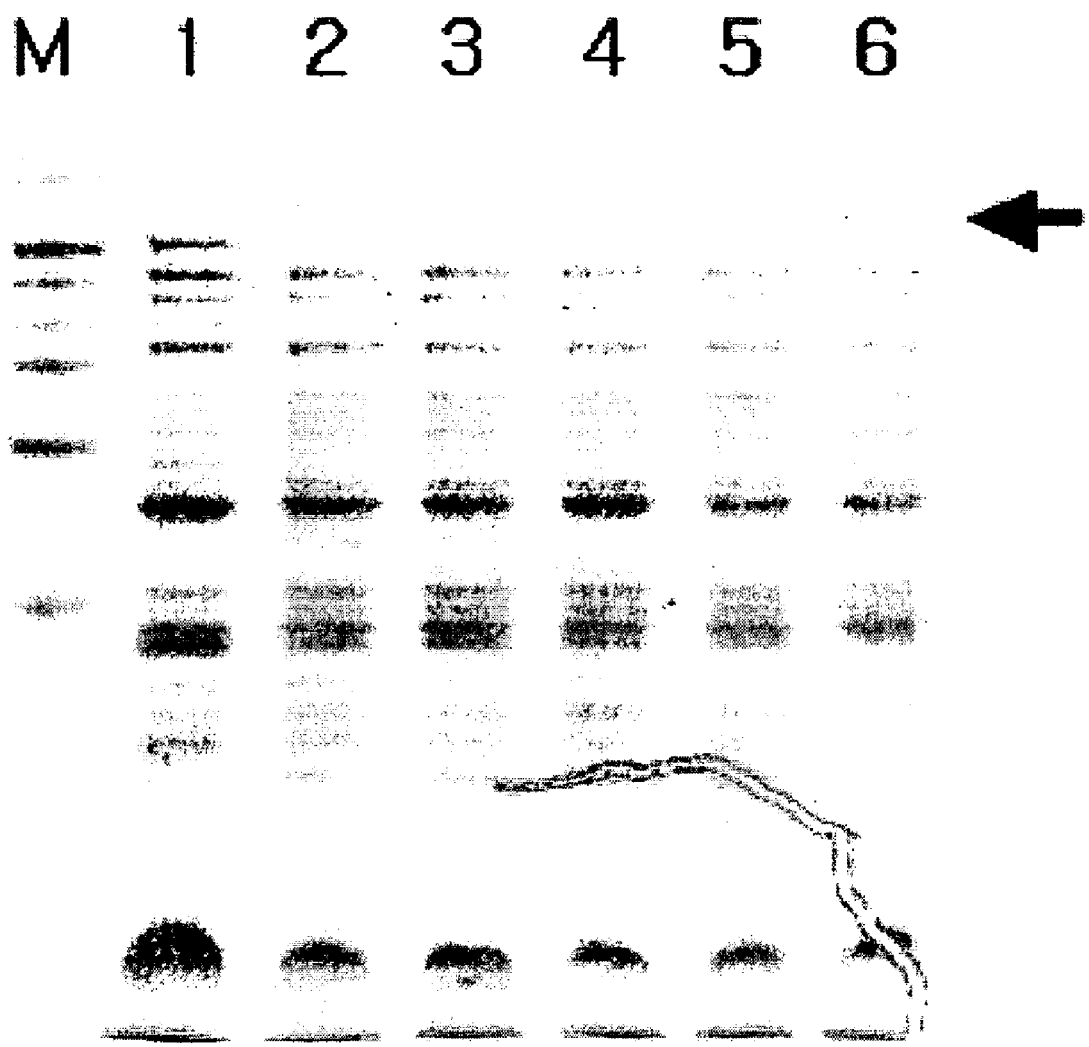
FIG. 6 shows the result of SDS-PAGE performed according to the Example 4 of the present invention depicting the level of β-glucosidase (indicated by arrows) synthesized by the induction of acs promoter in JM109 host cells transformed with pSS121 by culturing in LB medium wherein the LB medium is added with glucose.

To investigate whether the expression of β-galactosidase can be regulated when the β-galactosidase expression is induced by the acs promoter, the protein expression was analyzed by adding 4 g/L of glucose into an LB medium (FIG. 6). The level of β-galactosidase synthesis induced by the acs promoter is analyzed on SDS-PAGE as shown in FIG. 6.

Here, M is a protein size marker, 1 represents a sample obtained from a 2 hr culture, 2 for a sample obtained from a 4.5 hr culture, 3 for a sample obtained from a 5.5 hr culture, 4 for a sample obtained from a 7.5 hr culture, 5 for a sample obtained from an 11 hr culture, and 6 for a sample obtained from a 24 culture.

As shown in the result, the expression cultured in complex LB medium was completely inhibited when glucose was added.

Figure 7:
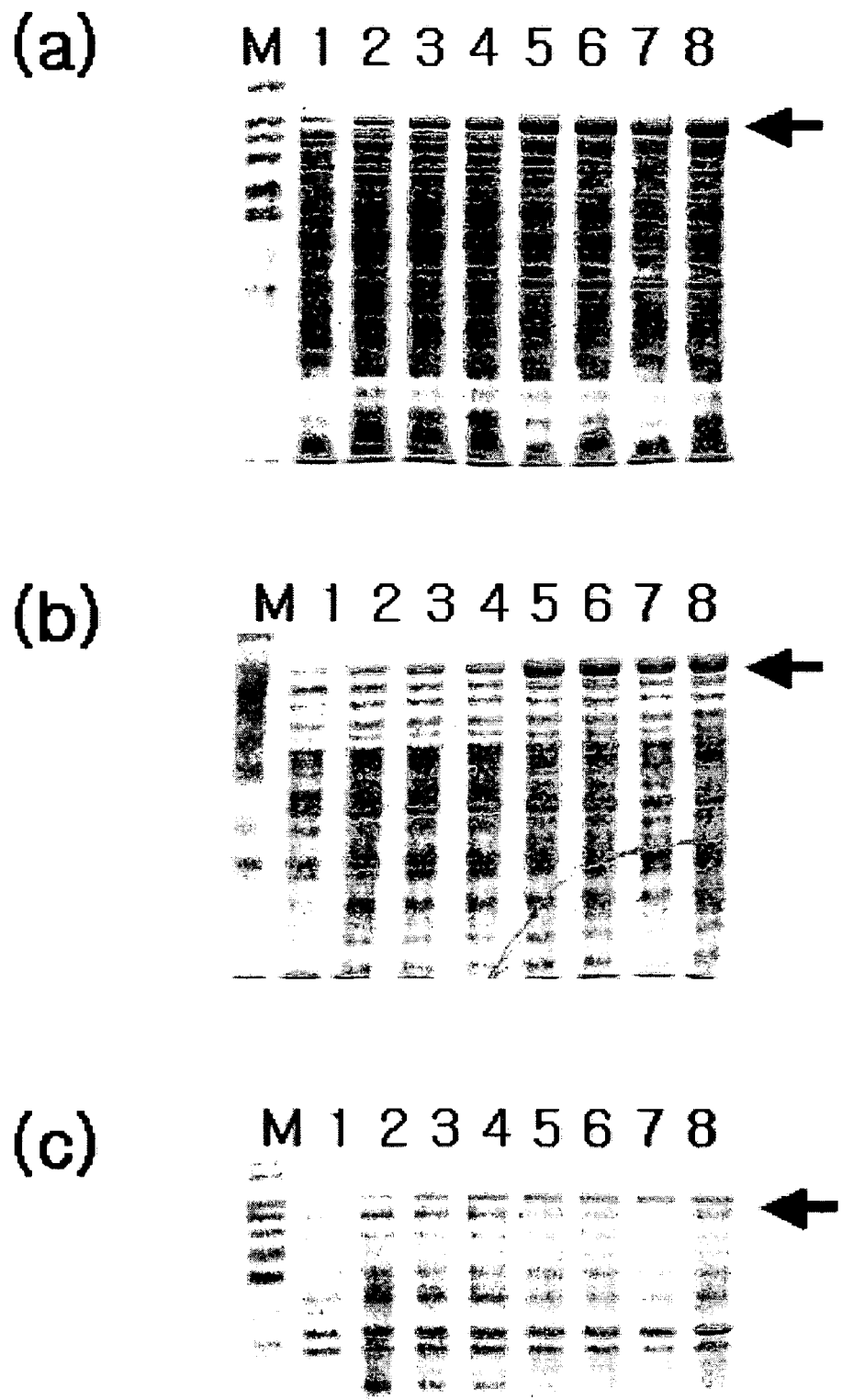
FIG. 7a shows the results of SDS-PAGE for the total cumulative proteins synthesized by the recombinant JM109, when cultured in M9 minimal culture medium, wherein glucose or succinic acid is used as a sole carbon source.
FIG. 7b shows the results of SDS-PAGE for a soluble protein fraction.
FIG. 7c shows the results of SDS-PAGE for an insoluble protein fraction.

FIG. 7 shows the amount of proteins synthesized when cultured in M9 minimal culture medium, wherein glucose or succinic acid was used as a sole carbon source. *E. coli* JM109 transformed with pSS121 was cultured in two different medium conditions of an M9 glucose medium (samples 1-4) and in an M9 succinic medium (samples 5-8), and the level of β-galactosidase synthesis induced by acs promoter as indicated by an arrow was analyzed on SDS-PAGE.

Here, FIG. 7(a) shows the total cumulative proteins synthesized by the recombinant JM109/pSS112, FIG. 7(b) shows the result for a soluble protein fraction and FIG. 7(c) shows the result for an insoluble protein fraction. Also, M is a protein size marker, 1 represents a sample obtained from a 4.5 hr culture in M9 glucose medium, 2 for a sample obtained from a 7 hr culture in M9 glucose medium, 3 for a sample obtained from a 12 hr culture in M9 glucose medium, 4 for a sample obtained from a 20 hr culture in M9 glucose medium, 5 for a sample obtained from a 4.5 hr culture in M9 succinic medium, and 6 for a sample obtained from a 7 hr culture in M9 glucose medium, 7 for a sample obtained from a 12 hr culture in M9 succinic medium, 8 for a sample obtained from a 20 hr culture in M9 succinic medium. As shown in FIG. 7, it was also revealed that protein expression was remarkably inhibited when using glucose as a sole carbon source.

The amount of protein synthesis was observed to be less than 2% of the total protein during the log phase, and approximately 10% of the total protein was accumulated in a cell during the resting stage. When used succinic acid as a carbon source, in contrast, more than 40% of the total protein was accumulated during the initial culturing stage of log phase and resting stage, and the proteins expressed were mostly soluble proteins.

Example 5

Figure 8:
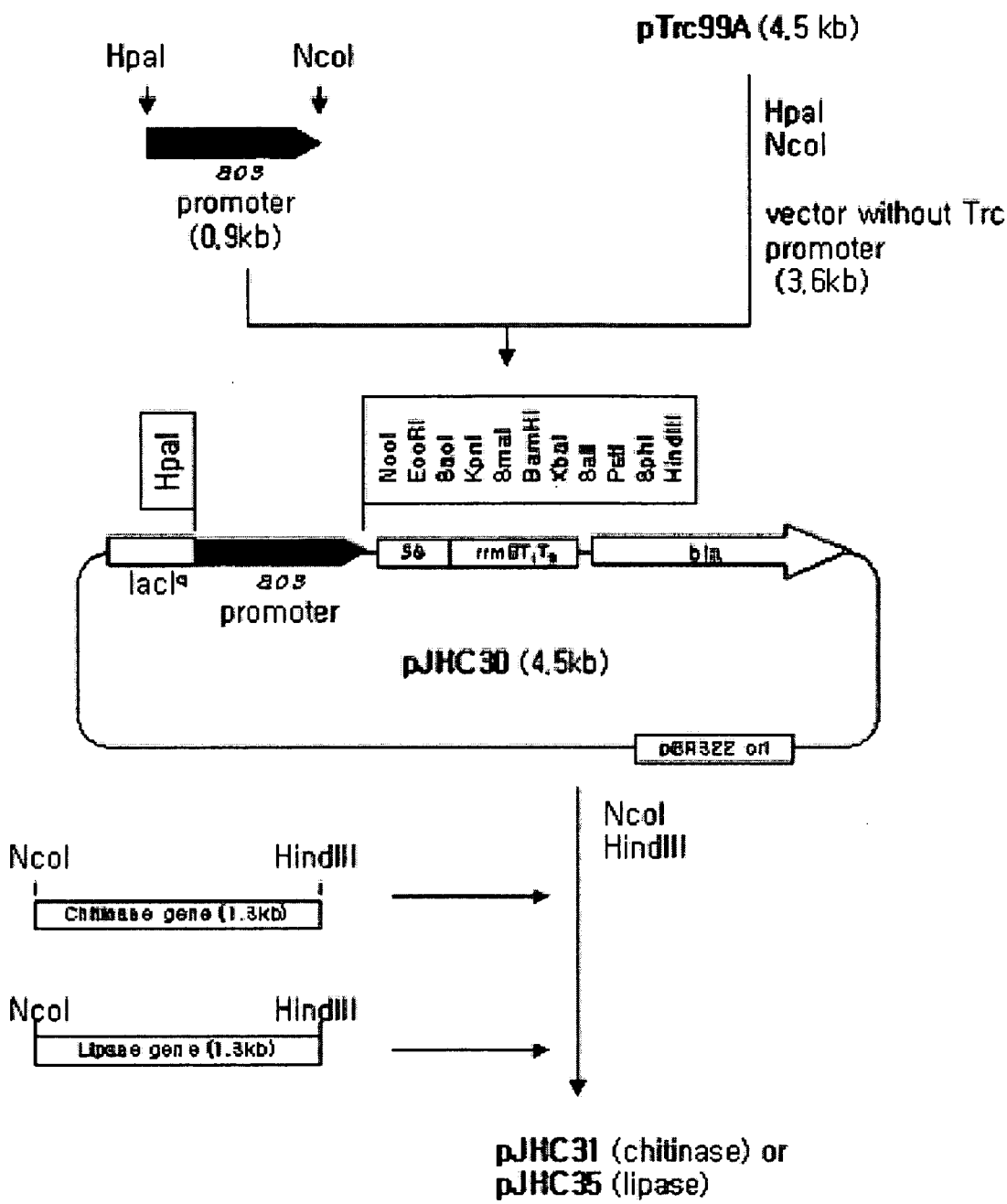
FIG. 8 is a schematic diagram showing the process of constructing pJHC30, a general expression vector constructed by subcloning only acs promoter, as well as pJHC31 and pJHC35 according to the Example 5 of the present invention, wherein chitinase gene and lipase gene are subcloned, respectively.

Construction of an Expression Vector pJHC30 for a Foreign Protein and the Expression of the Foreign Protein Induced by acs Promoter For the application of the expression system of the present invention to an expression of a foreign protein, an expression vector pJHC30 was constructed by replacing trc promoter present in pTrc99A, a conventional highly expressive vector for *E. coli*, with acs promoter by subcloning acs promoter via PCR technology and its usefulness was examined. In subcloning acs promoter, pSS112, which was used as a DNA template for acs promoter, was PCR amplified by using SEQ ID NO:4 and SEQ ID NO:5 were used as primers, respectively, digested with Hpa I and NcoI and then subcloned into pTrc99A, also digested with the same restriction enzymes (FIG. 8). Thus constructed pJHC30 was transformed into JM109 and the resulting JM109/pSS121 was cordially deposited with the Korea Research Institute of Bioscience and Biotechnology Korean Collection for type cultures, Korean Deposit Associates, located in #52, Oun-dong, Yusung-gu, Daejon, 305-333, Republic of Korea, on Dec. 15, 1999, under Deposit Accession Number KCTC 0712BP. However, the use of pTrc99A is intended to exemplify the usefulness of acs promoter and the use of a useful vector thus should not be restricted to pTrc99A.

As a step toward the expression of a protein by acs promoter, about 1.3 kb chitinase gene derived from *Serratia marcescens* ATCC 27117 and about 1.3 kb of lipase gene derived from *Peudomonas fluorescens* SIK W1 (Ahn et al, 1998, *J. Bacteriol.*, 181, 1847-1852) were subcloned into pJHC31 and pJHC35 (FIG. 8), respectively. The above pJHC31 and pJHC35 were transformed into *E. coli* JM109 and proteins were expressed. The results were analyzed on SDS-PAGE as shown in FIGS. 9 and 10.

Figure 9:
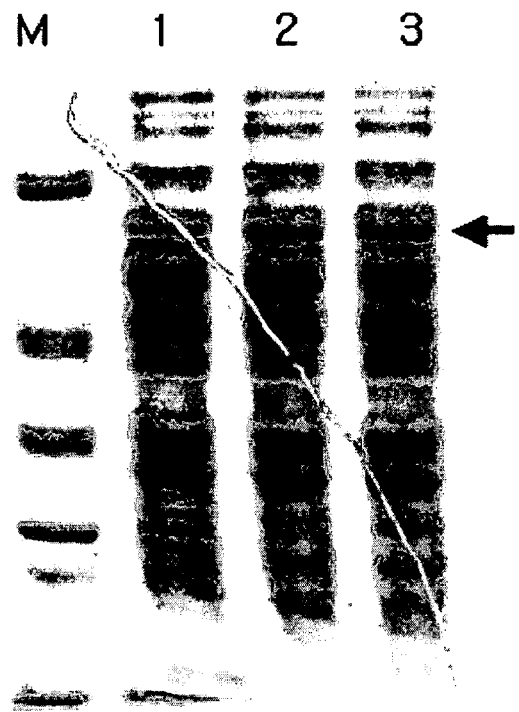
FIG. 9 is the result of SDS-PAGE performed according to the Example 5 of the present invention showing the level of chitinase (indicated by an arrow) expressed by pJHC31.

In FIG. 9, M is a protein size marker, 1 represents a sample of the total JM109 protein, 2 is a sample obtained from a 20 hr culture in LB medium, and 3 is a sample obtained from a 20 hr culture in M9 minimal succinic medium.

Figure 10:
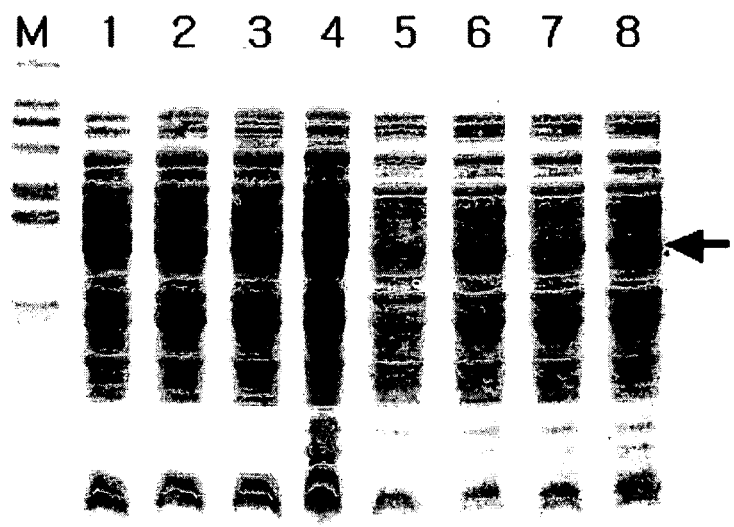
FIG. 10 is the result of SDS-PAGE performed according to the Example 5 of the present invention showing the level of lipase (indicated by an arrow) expressed by pJHC35.

FIG. 10 shows the result of lipase expression via pJHC35 analyzed on SDS-PAGE. In FIG. 10, M is a protein size marker, 1 represents a sample obtained from a 7 hr culture in LB medium, 2 for a sample obtained from a 9 hr culture in LB medium, 3 for a sample obtained from a 12 hr culture in LB medium, 4 for a sample obtained from a 24 hr culture in LB medium, 5 for a sample obtained from a 6.5 hr culture in M9 succinic medium, 6 for a sample obtained from an 8.5 hr in M9 succinic medium, 7 for a sample obtained from a 12.5 hr culture in M9 succinic medium, 8 for a sample obtained from a 24 hr culture in M9 succinic medium.

As described earlier, the protein expression reached about 16% of the total protein of *E. coli* in case of chitinase while the protein expression reached about 5% in the case of lipase, which is generally not well expressed in *E. coli*.

Example 6

Construction of the Artificial Promoters Consisting of Modified acs Promoters and Tandem Repeating Promoters and its Application for Expressing an Aminase (guaA) from *Escherichia coli*

Figure 11:
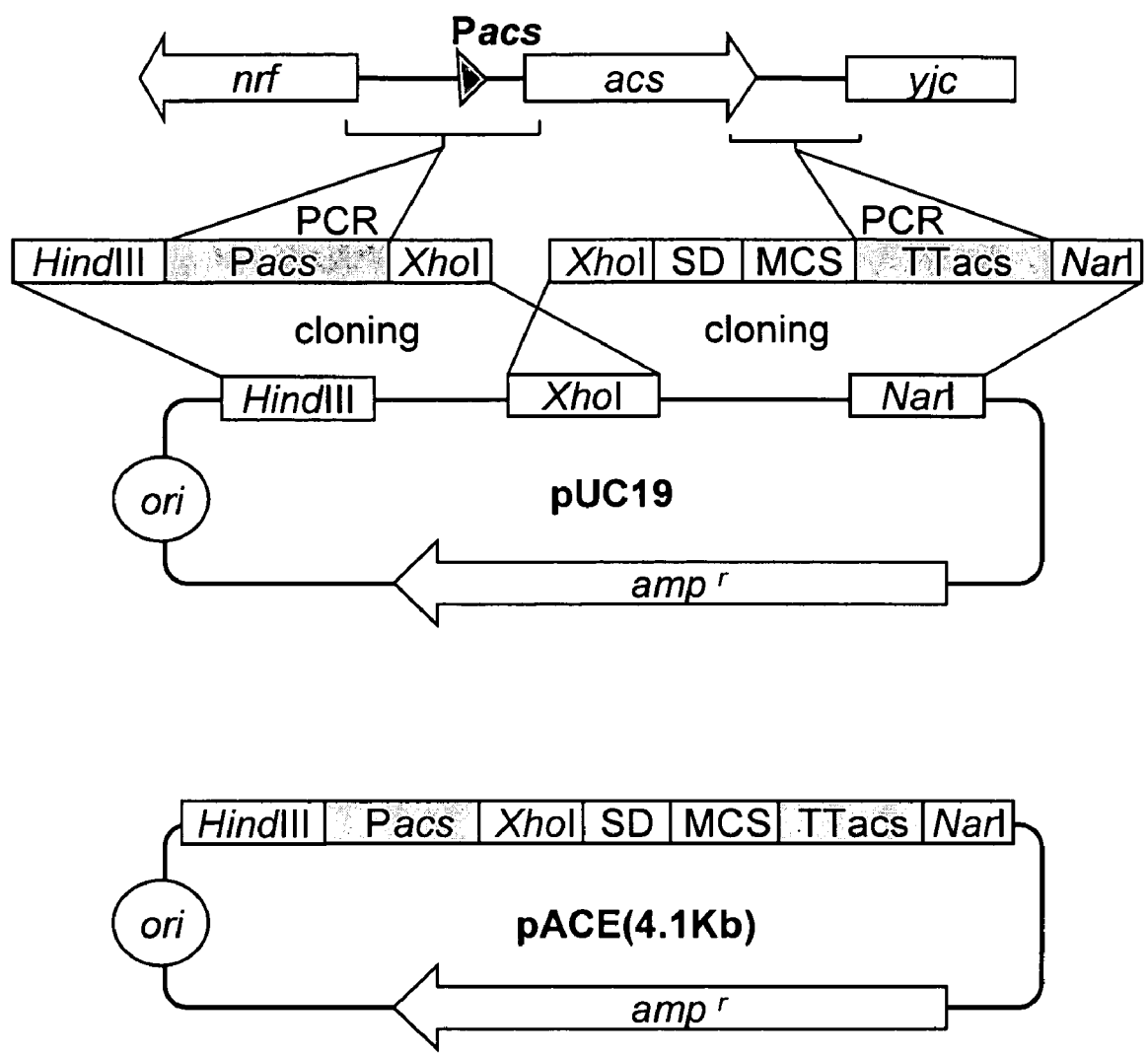
FIG. 11 is a schematic diagram showing the process of constructing pACE, a general expression vector constructed by subcloning only acs promoter.

Plasmid pACE consists of acs promoter region, acs terminator region and pUC19-based replication origin. To construct plasmid pACE, the acs promoter including the first 120 nucleotides of the acs structure gene and the acs terminator were amplified by PCR using K-12 *E. coli* chromosomal DNA as a template and primers Pacs5 (CGAAGCTTATCGATTGCTGGTCGAAAC), Pacs3 (CCGCTCGAGCAGGGTATTGGCGAAGCG GCAGAC), Tacs5 (CCGCTCGAGAATAAGAAGGAGATATACATATGATATAC ATATGGAATTCCC CGGGATCCCTGCAGGGTAC-CGAGCTCAGGCTATCGCGATGCCATCGTAAC), and Tacs3 (GACACTACTTACCGTGATAAATAGTCGCCCGCGGCGCG), which contained HindIII, XhoI, XhoI and NarI restriction sites (underlined), respectively. The PCR product containing the acs promoter region was digested with HindIII and XhoI and cloned into pUC19 plasmid digested with the same restriction enzymes, and named plasmid pUC19-acs. The acs terminator region was amplified using primer Tacs5 which includes the Shine-Dalgarno (SD) box, multi-cloning sites and 18 bp of acs gene 3' end. The PCR product was cloned into XhoI and NarI restriction enzyme sites of pUC19-acs plasmid, resulting pACE expression vector (FIG. 11).

The lacZ gene was amplified by PCR using pMC1871 (Amersham Biosciences, Piscataway, N.J.) as a template with the upstream primer GGAATTCCATATGGTCGTTTTACAACGTCGTGAC and downstream primer AACTGCAGTCCCCCCTGCCCGGTTAT which contained NdeI and PstI restriction sites (underlined), respectively, and subcloned into the same sites of pACE.

Figure 12:
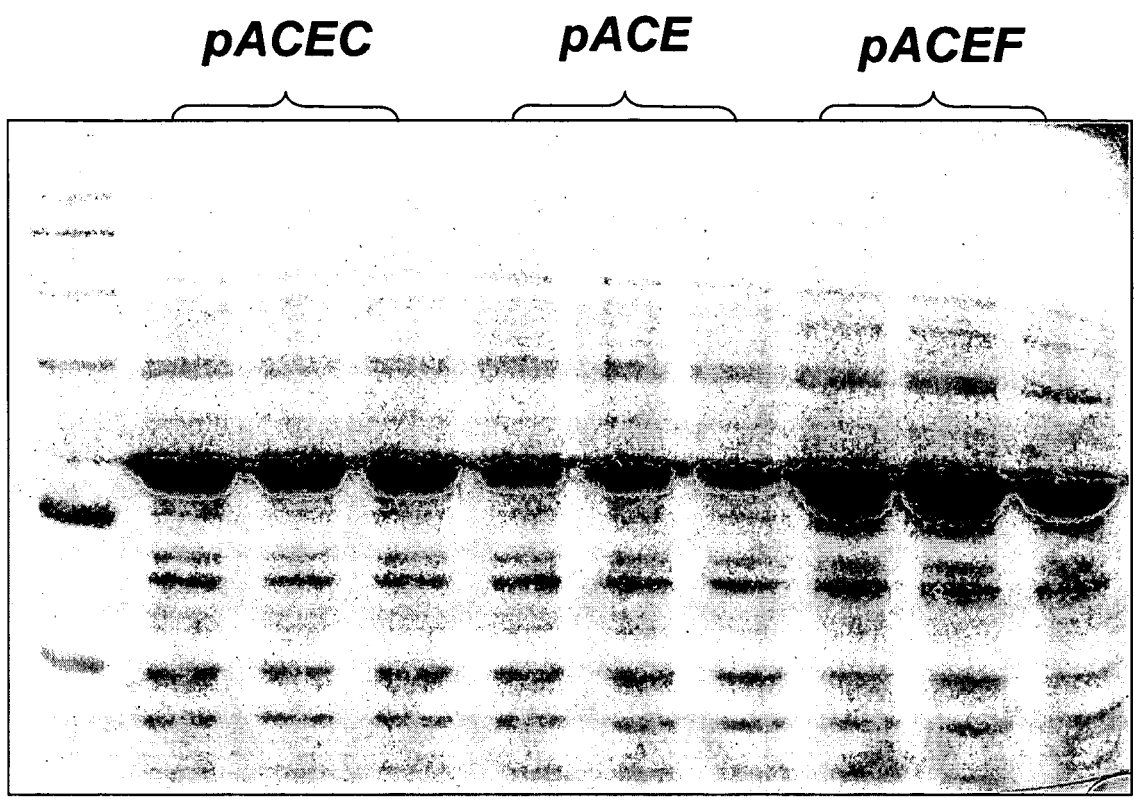
FIG. 12 is the result of SDS-PAGE performed according to the Example 6 of the present invention showing the level of aminase (indicated by an arrow) expressed by pACE, pACEC and pACEF vectors.

Plasmid pACE-GFPuv (containing the gfpuv gene under control of the acs promoter) was constructed by placing a 0.7 kb PCR fragment including an gfpuv gene into Pace vector. The gfpuv gene was amplified by PCR using pGFPuv vector (Clontech, Palo Alto, Calif.) as template. The primer sequences were upstream primer TGAGTAAAGGAGAAGAACTTTTC and downstream primer AACTGCAGTCATTATTTGTACAG. The amplified DNA fragments were digested with PstI and inserted into the pACE vector treated NdeI, klenow fragment and PstI serially. pACEC which contains modified acs promoter was also constructed. To construct the modified acs promoter, the CRP (catabolite repressor protein) binding site was removed, thus, no glucose repression, generating a constitutive promoter. The another novel expression vector pACEF was also constructed by fusing wildtype acs promoter from pACE with the CRP site removed promoter from pACEC. In order to test their expression capability, the guaA gene encoding an aminase from *E. coli* was subcloned into pACE, pACEC, and pACEF vectors. The expression results are shown in FIG. 12. pACEF gave a very high level of target proteins without any chemical inducers.

Example 7

Expression in *E. coli* of a Catalase in High Cell Density Culture

Figure 13:
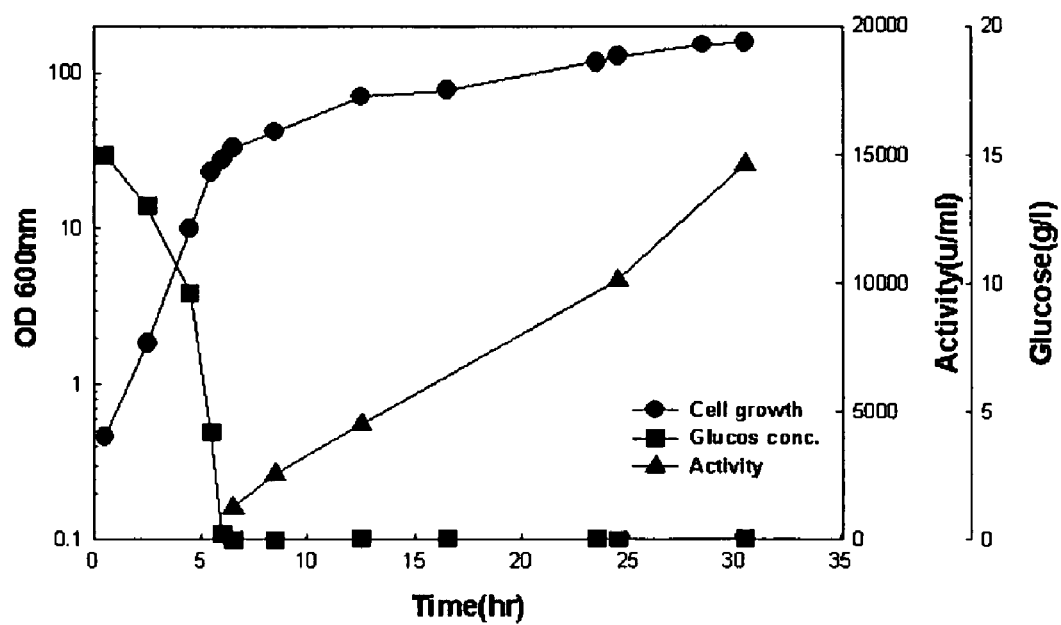
FIG. 13 is the result of high cell density cultivation for overexpression of catalase according to Example 7.

In order to overproduce a catalase (katE) from *E. coli*, the katE gene (2262 bp) was subcloned into the pACEF vector. *E. coli* host cells containing the resulting vector were cultivated more than 120 of optical density at 600 nm (40 dried cells/liter) by feeding glucose as carbon and energy substrate as shown in FIG. 13. Glucose was maintained at less than 0.1 g/L by feeding glucose slowly with 20%-30% of maximum specific growth rate. Initiation of synthesis of target proteins (catalase) was started by entering stationary phase after glucose was depleted. Simultaneously, feeding of glucose was started. Finally, after 24 hours of glucose feeding and synthesis of target proteins, more than 1 g/L of catalase was obtained.

As described above, the protein expression system of the present invention enables a transformed host cell to effectively synthesize a protein. Further, the method to induce protein expression of the present invention is not only able to regulate the expression with an added precision but is also shown advantageous in that the inducers are various in its kinds, the inductive activities are not affected by the impurities contained, and they are also able to induce an instant expression even in a large-scale cell culture. More specifically, the method of the present invention can induce protein expression during the resting stage of cell growth thus preventing the generation of inclusion bodies and expressing more amount of a soluble protein.

What is claimed is:

1. A method of producing a desired protein by gene recombination at a host cell culture density of at least 40 g/L, the method comprising the steps of:
    (a) constructing a gene expression vector comprising a gene that encodes the desired protein and a gene that contains a DNA fragment selected from the group consisting of acs gene, lac Z gene, chiA gene and tliA gene, said gene being operably linked to an inducible acs promoter,
    (b) introducing said gene expression vector into the host cell;
    (c) inducing the expression of said desired protein by culturing said host cell in culture medium and adding acetic acid or succinic acid; and
    (d) recovering the desired protein from the culture.

2. The method according to claim 1, wherein said promoter includes a 1 kb DNA fragment that contains the acs promoter of *E. coli*.

3. The method according to claim 1, wherein said host cell is Gram-negative bacteria.

4. The method according to claim 1, wherein said culture medium is selected from the group consisting of a complex medium, a minimal culture medium containing acetic acid or succinic acid as a sole carbon source, and a minimal medium containing glucose or glycerol as a sole carbon source.

5. The method according to claim 4, wherein said culture medium is the minimal medium containing glucose or glycerol as a sole carbon source and wherein said culture medium contains either acetic acid or succinic acid as an inducer.

6. The method according to claim 1, wherein the host cell density is greater than 100 g/L.

7. The method according to claim 1, wherein the expression of said desired protein is induced by feeding a carbon source at a limited rate to maintain the specific growth rate lower than the maximum value.

8. The method according to claim 7, wherein the carbon source is selected from the group consisting of glucose, fructose, galactose, lactose, sucrose, maltose, glycerol, formic acid, acetic acid, propionic acid, butyric acid, succinic acid, fumaric acid, malic acid and citric acid.

* * * * *

SEQUENCE LISTING

```
<160> NUMBER OF SEQ ID NOS: 5

<210> SEQ ID NO 1
<211> LENGTH: 1384
<212> TYPE: DNA
<213> ORGANISM: Artificial Sequence
<220> FEATURE:
<223> OTHER INFORMATION: Description of Artificial Sequence: pSK122
      Plasmid

<400> SEQUENCE: 1
atcgattgct ggtcgaaacg tccggctttc tcaaaaggtt taccaatggc ttccatcgcg      60
cgagccgcat acggacggga aagggttaac tccggtttgc ctttggcgaa ctctggagag     120
```

-continued

```
gcggtgttat ggcaatcggc acaacctaag ttgttgacga tttccggacc gccgcgcgcc      180
catttaccgt ggaagtagcc atcttcgccg tctttctgga tcagacgcgc cacatccggg      240
cttttacaac tccagcatgc catcggtagc ggaccatctt cagcgttttt cggcgcaccg      300
gtacgcaggg tttcacgcac atcggtcaca gcaaaagcat gtccacgcgg cttgttgtaa      360
tcgcgcgaga agggataccc cgcccacagg atcaccagcc gtggatcttc cgcagggcg       420 tcaacacgct ctgactgttc cgaggtggct ttccaggaga gatattgatc gggatgctgc      480
ggggcaaagg tttcattctt cgcttccaca gttacaggtt ttgcgggagc agccgtttgt      540
tcagcgtgaa cagaagtgaa aaagaaaaaa ggaatcaata agctgaagat acggcgtgcg      600
tttattttta tccttgtcat aggggcttca tccgaattgc gccattgttg caatggcggt      660
ttttattgtt tttcacgaca gtaaccgcac ctacactgtc atgacattgc tcgccctat      720 gtgtaacaaa taaccacact gtgaatgttg tctttaatca attgtaagtg catgtaaaat     780
accactttag agttagtcag tatcttcctc tttttcaaca gcatgcataa ctgcatgttc      840
ctcaaagaat taatcaactt tgttgctga ccttcaaaaa ttaccctgcc gtttatttgc       900
acaattctac ttttgcgtga tctgtcgccc aaatactaaa caaaactgcc aatacccta      960 catttaacgc ttatgccaca tattattaac atcctacaag gagaacaaaa gcatgagcca     1020
aattcacaaa cacaccattc ctgccaacat cgcagaccgt tgcctgataa accctcagca     1080
gtacgaggcg atgtatcaac aatctattaa cgtacctgat accttctggg gcgaacaggg    1140
aaaaattctt gactggatca aaccttacca gaaggtgaaa aacacctcct ttgccccgg      1200 taatgtgtcc attaaatggt acgaggacgg cacgctgaat ctggcggcaa actgccttga    1260
ccgccatctg caagaaaacg cgatcgtac cgccatcatc tgggaaggcg acgacgccag     1320
ccagagcaaa catatcagct ataaagagct gcaccgcgac gtctgccgct cgccaatac    1380 cctg                                                                  1384
```

```
<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 2
tcgaggtcga cggtatc                                                     17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
cgctctagaa ctagtggatc                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
gacgggaaag ggttaactcc                                                  20
```

```
<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
tttggcccat ggttttgttc tcc                                            23
```